United States Patent [19]

Rigby

[11] Patent Number: 5,324,876
[45] Date of Patent: Jun. 28, 1994

[54] CATALYTIC METAL PROMOTED CYCLOADDITION PROCESS

[75] Inventor: James H. Rigby, West Bloomfield, Mich.

[73] Assignee: Wayne State University, Mich.

[21] Appl. No.: 109,608

[22] Filed: Aug. 19, 1993

Related U.S. Application Data

[63] Continuation of Ser. No. 943,053, Sep. 10, 1992, abandoned.

[51] Int. Cl.$^5$ .................... C07C 2/00; C07C 13/28
[52] U.S. Cl. ............................... 585/360; 585/361
[58] Field of Search ............................. 585/360, 361

[56] References Cited

PUBLICATIONS

Rigby et al., J. Am. Chem. Soc. (1990), vol. 112, pp. 6442–6443.
Rigby et al., J. Am. Chem. Soc. (1991), vol. 113, pp. 5122–5123.

*Primary Examiner*—Asok Pal
*Attorney, Agent, or Firm*—Marshall & Melhorn

[57] ABSTRACT

Small catalytic amounts of a transition metal catalyst such as Cr(O) are used in a higher order cycloaddition process in which a triene is reacted with a diene or alkene to efficiently and economically provide a cycloaddition product.

32 Claims, No Drawings

CATALYTIC METAL PROMOTED CYCLOADDITION PROCESS

This is a continuation of copending application Ser. No. 07/943,053, filed on Sep. 10, 1992, now abandoned.

The present invention is directed to a transition metal promoted cycloaddition process comprising reacting a triene and a diene or alkene to produce bicyclic cycloaddition products.

BACKGROUND OF THE INVENTION

Higher-order cycloaddition processes are known in which transition metal mediated or transition metal templates are used in which the transition metal catalyst is used in stoichiometric amounts to provide cycloaddition products.

Publications are as follows:

1 Rigby and Ateeq, "Synthetic Studies on Transition-Metal-Mediated Higher Order Cycloaddition Reactions: Highly Stereoselective Construction of Substituted Bicyclo [4 4 1]undecane Systems" *Journal of the American Chemical Society*, 1990, 112.

2 Rigby and Henshilwood, "Transition Metal Template Controlled Cycloaddition Reactions. An Efficient Chronium(0)-Medicated [6π+2π] Cycloaddition", *Journal of the American Chemical Society*, 1991, 113.

The above publications, directed to the use of transition metal catalysts only in stoichiometric amounts, are incorporated by reference for their disclosure of triene, dienes and transition metal compounds including. chromium (0) complexes used in the transition metal mediated cycloaddition reactions.

It is desirable to provide an efficient cycloaddition process using only a small catalytic quantity of the expensive transition metal.

OBJECTS OF THE INVENTION

It is an object of the present invention to provide a cycloaddition process in which a transition metal catalyst is used in small, catalytic amounts instead of stoichiometric amounts, to react a triene and a diene or alkene.

It is an object of the present invention to provide a process of reacting an organic triene having a 7-membered ring structure with a diene or an alkene in the presence of about 2 to 15 mole %, based on the triene of a transition metal catalyst, to provide a bicyclo cycloaddition product, there being about 1 to 1.5 equivalent weights of the diene or alkene per one equivalent weight of triene.

It is an object of the present invention to provide a cycloaddition process as above described in which the triene is tropone, the diene is a 1, 4- substituted butadiene, and the catalyst is a chromium compound that forms a complex with tropone.

These and other objects of the invention will be apparent from the specification that follows and the appended claims.

SUMMARY OF THE INVENTION

The present invention provides an efficient process using only small catalytic amounts of the expensive transition metal compound catalysts, the cycloaddition reaction being a process of reacting an organic triene having a 7-member ring structure with a diene or an alkene in the presence of about 2 to 15 mole %, based on the triene plus diene or alkene, of a transition metal catalyst, to provide a bicyclo cycloaddition product, there being about 1 to 1.5 equivalent weights of the diene per one equivalent weight of triene.

In the above process, the preferred range of equivalent weights of diene is about 1.1 to 1.3 to one equivalent weight of triene.

Instead of large stoichiometric amounts of the transition metal catalysts, only a small amount of catalyst is used, generally about 2 to 15 moles of catalyst per 100 moles of diene and triene reactants. Preferably, the amount of catalyst is about 5 to 10 mole%.

Preferred trienes are tropone and cycloheptatriene including 7-substituted cycloheptatriene in which the substituent is an N atom, a $CO_2CH_2$ group or an $SO_2$ group. Also preferred are 1-, or 2-, or 3- substituted cycloheptratrienes.

Suitable trienes are those of the formula

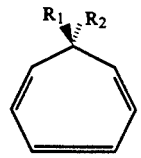

where $R_1$ and $R_2$ are both H or are H and OMe, or Me and H or both OMe where Me is methyl. Also suitable trienes are:

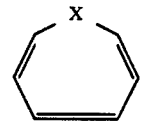

where $X=NCO_2R$; $X=SO_2$

Suitable trienes are also of the formula

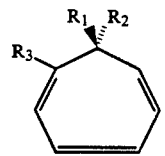

where $R_1$;$R_2$ and $R_3$ are H; or $R_1$ and $R_2$ and H and $R_3$ is OMe; or $R_1$ is Me, $R_2$ and $R_3$ are H.

Suitable dienes are those of the formula:

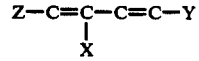

where Y and Y are H and Z is OMe or where at least one of X, Y and Z is H and the other two substituents are Me, OMe, $CO_2$ Me or acetoxy.

Preferred dienes are 1,4 substituted butadienes including 1,4-diacetoxybutadiene, or dimethyl muconate.

The diene can be substituted in whole or part by an alkene, preferably diethyl maleate or a —$CO_2$Et substituted alkene where Et is ethyl. Also preferred is ethyl acrylate, methyl acrylate, methoxy acrylate or butoxy acrylate.

Suitable alkenes are of the formula:

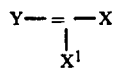

where the X, X¹, and Y substituents are H, COMe, CO₂, Et, CN, or OBu, at least one or preferably two of the substituents being H.

The preferred transition metal is chromium. Excellent results are obtained using nickel or cobalt. Suitable transition metals are copper, vanadium and titanium.

The preferred catalysts are transition metal compounds, preferably chromium compounds that form a complex with the triene or with arenes such as benzene, naphthalene, anthracene and their derivatives. A preferred catalyst is Cr(O).

In the present invention, the outstanding product, produced by the efficient, economical process, is a $(6\pi+2\pi)$ cycloaddition product.

In the present invention, the process includes heating a solution of the triene chromium tricarbonyl complex with a diene or alkene at 150° C. for 12 to 24 hours.

The following equations illustrate the cycloaddition reactions:

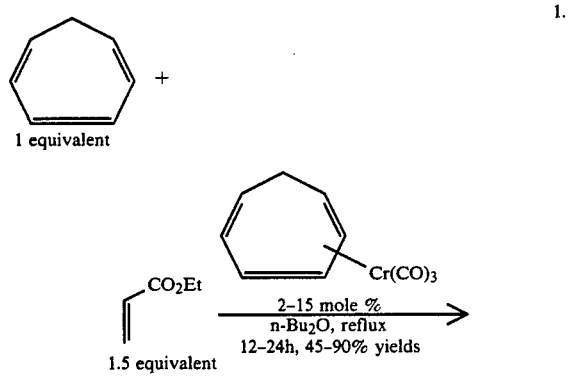

1.

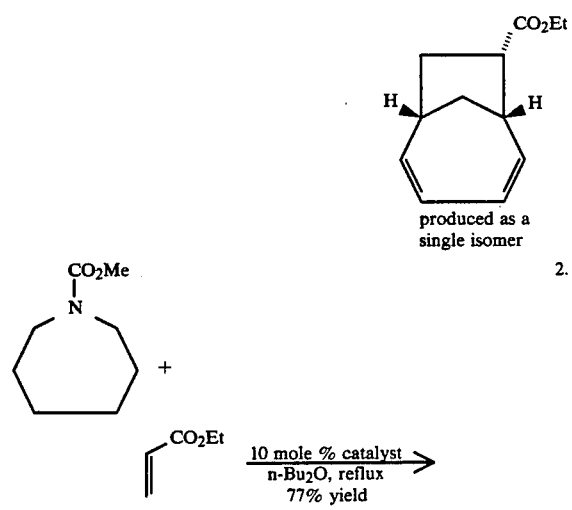

2.

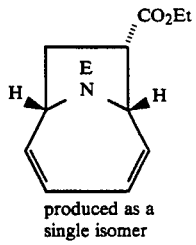

produced as a single isomer

The above equations illustrate the efficient economical cycloaddition process of the present invention in which only catalytic amounts of metal are used where E=COOMe.

What is claimed is:

1. A process of reacting an organic triene having a 7-member ring structure with a diene or an alkene in the presence of about 2 to 15 mole %, based on the triene of a transition metal catalyst, under the refluxing conditions of the reaction mixture to provide a bicyclo cycloaddition product, there being about 1 to 1.5 moles of the diene or alkene per one mole of triene.

2. A process as defined in claim 1 in which the triene is cycloheptatriene.

3. A process as defined in claim 1 in which the triene is a 7-substituted cycloheptatriene.

4. A process as defined in claim 1 in which the triene has a N atom in the 7 position and a CO₂ CH₃ group attached to the N atom as a substituent.

5. A process as defined in claim 1 in which the triene has an SO₂ group in the 7 position.

6. A process as defined in claim 1 in which the triene is tropone.

7. A process as defined in claim 1 in which the diene is a 1, 4 substituted 1, 3-butadiene.

8. A process as defined in claim 1 in which the diene is dimethyl muconate.

9. A process as defined in claim 1 in which the alkene has a-CO₂ Et substituent, where Et is ethyl.

10. A process as defined in claim 1 in which the alkene is diethyl maleate.

11. A process as defined in claim 1 in which the alkene is ethyl acrylate.

12. A process as defined in claim 1 in which the diene or alkene is about one mole.

13. A process as defined in claim 1 in which the diene or alkene is about 1.5 moles.

14. A process as defined in claim 1 in which the catalyst is a chromium catalyst.

15. A process as defined in claim 1 in which the transition metal is nickel.

16. A process as defined in claim 1 in which the transition metal is copper or titanium.

17. A process as defined in claim 1 in which the catalyst is Cr (CO)₃.

18. A process as defined in claim 1 in which the catalyst is a chromium compound that forms a complex with the triene.

19. A process as defined in claim 1 in which the catalyst is an arene-Cr(CO)₃ complex.

20. A process as defined in claim 1 in which the catalyst is Cr (0).

21. A process as defined in claim 1 in which the product is a $(6\pi+2\pi)$ cycleaddition product.

22. A cycleaddition process as follows:

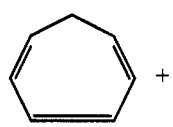 +

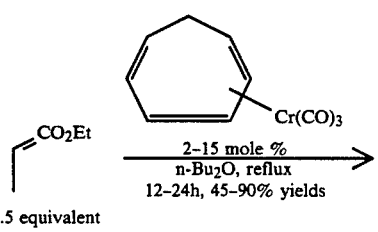

1 equivalent 1.5 equivalent

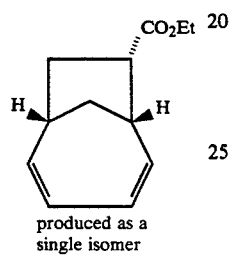

produced as a single isomer

23. A cycleaddition process as follows:

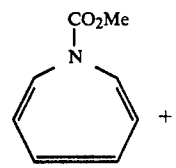 +

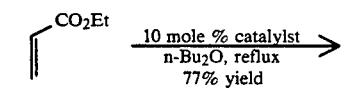

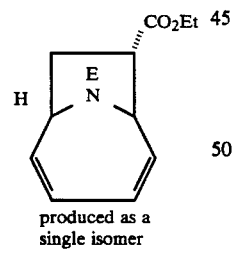

produced as a single isomer

24. A process as defined in claim 1 in which the triene is a 1-substituted cycloheptatriene.

25. A process as defined in claim 1 in which the triene is a 2-substituted cycloheptatriene.

26. A process as defined in claim 1 in which the triene is a 3-substituted cycloheptatriene.

27. A cycloaddition process comprising the steps of:
a) reacting about 1 equivalent of

and about 1.5 equivalents of

by refluxing for about 12 to 24 hours in n-Bu$_2$O with about 2-15 mole % of Cr(CO$_3$ as a catalyst to provide

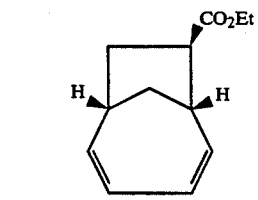

at a yield of about 45-90%.

28. A cycloaddition process comprising the following steps:

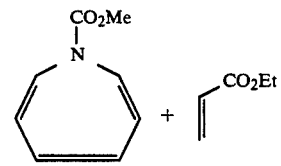

with about 10 mole % of Cr(CO)$_3$ as a catalyst under the refluxing conditions of the reaction mixture to form

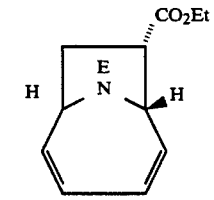

produced as a single isomer at about 77% yield.

29. A process as defined in claim 27 in which the catalyst is a triene chromium tricarbonyl complex.

30. A process as defined in claim 27 in which about 10 mole % of the catalyst is used and which n-butyl ether is a solvent that provides for recovery and recycling the metal catalyst.

31. A process as defined in claim 27 in which a solvent equivalent to Bu$_2$O is used to dissolve the Cr(CO$_3$) catalyst and recycle the catalyst.

32. A process as defined in claim 28 in which a solvent equivalent to n-Bu$_2$O is used to dissolve and recycle the catalyst.

* * * * *